United States Patent
Mason et al.

(10) Patent No.: US 12,042,652 B2
(45) Date of Patent: **\*Jul. 23, 2024**

(54) ELECTRICAL CURRENT STIMULATOR APPARATUS

(71) Applicant: ZIIP, INC., Oakland, CA (US)

(72) Inventors: David Mason, Oakland, CA (US); Melanie Simon, Oakland, CA (US); Ron Lisiecki, Oakland, CA (US)

(73) Assignee: ZIIP, INC., Pleasant Hill, CA (US)

( * ) Notice: Subject to any disclaimer, the term of this patent is extended or adjusted under 35 U.S.C. 154(b) by 405 days.

This patent is subject to a terminal disclaimer.

(21) Appl. No.: 17/188,598

(22) Filed: Mar. 1, 2021

(65) Prior Publication Data

US 2021/0178159 A1 Jun. 17, 2021

Related U.S. Application Data

(63) Continuation of application No. 15/855,282, filed on Dec. 27, 2017, now Pat. No. 10,967,180, which is a
(Continued)

(51) Int. Cl.
*A61N 1/36* (2006.01)
*A61H 23/02* (2006.01)
(Continued)

(52) U.S. Cl.
CPC ..... *A61N 1/36021* (2013.01); *A61H 23/0263* (2013.01); *A61N 1/0452* (2013.01);
(Continued)

(58) Field of Classification Search
CPC .............. A61N 1/36021; A61N 1/0452; A61N 1/0456; A61N 1/328; A61N 1/37282;
(Continued)

(56) References Cited

U.S. PATENT DOCUMENTS 4,699,143 A 10/1987 Dufresne et al.
5,304,207 A 4/1994 Stormer
(Continued)

FOREIGN PATENT DOCUMENTS

| IT | NA2014U000013 | * | 5/2015 |
| NA | 2014U000013 | * | 5/2014 |
| WO | 2015170241 A1 | | 11/2015 |

OTHER PUBLICATIONS

International Search Report and Written Opinion for PCT Application PCT/US2022/023581 issued on Jun. 10, 2022, 9 pages.
(Continued)

*Primary Examiner* — Mark W. Bockelman
(74) *Attorney, Agent, or Firm* — Polsinelli PC

(57) ABSTRACT

A method for providing electrical current treatment by an apparatus having a first electrode, a second electrode, and a processor is provided. The method includes delivering an electric current through an object in contact with the first electrode and the second electrode; controlling, by the processor, the electric current delivered by the first electrode and the second electrode to have a specific waveform; and providing a notification at a predetermined time to notify a user to move the apparatus.

20 Claims, 5 Drawing Sheets

Related U.S. Application Data continuation of application No. 14/587,638, filed on Dec. 31, 2014, now Pat. No. 9,861,818.

(51) Int. Cl.
- *A61H 39/00* (2006.01)
- *A61N 1/04* (2006.01)
- *A61N 1/32* (2006.01)
- *A61N 1/372* (2006.01)

(52) U.S. Cl.
CPC .......... *A61N 1/0456* (2013.01); *A61N 1/328* (2013.01); *A61N 1/37282* (2013.01); *A61H 39/002* (2013.01); *A61H 2201/0153* (2013.01); *A61H 2201/0188* (2013.01); *A61H 2201/5038* (2013.01); *A61H 2201/5097* (2013.01)

(58) Field of Classification Search
CPC .............. A61H 23/0263; A61H 39/002; A61H 2201/0153; A61H 2201/0188; A61H 2201/5038; A61H 2201/5097

See application file for complete search history.

(56) References Cited

U.S. PATENT DOCUMENTS

| | | |
|---|---|---|
| 6,007,532 A | 12/1999 | Netherly |
| 6,338,170 B1 | 1/2002 | Fiorentino |
| D466,217 S | 11/2002 | Harris et al. |
| 6,477,410 B1 | 11/2002 | Henley et al. |
| 6,766,199 B2 | 7/2004 | Cook et al. |
| D517,218 S | 3/2006 | Kalen |
| 7,083,580 B2 | 8/2006 | Bernabei |
| 7,141,031 B2 | 11/2006 | Garth et al. |
| D539,917 S | 4/2007 | Park |
| 8,469,906 B2 | 6/2013 | Milne et al. |
| 8,475,507 B2 | 7/2013 | Dewey et al. |
| 8,505,556 B2 | 8/2013 | Park et al. |
| 8,523,791 B2 | 9/2013 | Castel |
| 9,844,682 B2 | 12/2017 | Lisdhinsky et al. |
| 9,861,818 B2 | 1/2018 | Mason et al. |
| 10,967,180 B2 * | 4/2021 | Mason .................. A61N 1/328 |
| 2004/0260359 A1 | 12/2004 | Osrud |
| 2009/0048557 A1 * | 2/2009 | Yeshurun ............. A61B 18/203 604/20 |
| 2009/0048642 A1 | 2/2009 | Goroszeniuk |
| 2013/0000670 A1 * | 1/2013 | Binner ............... A46B 15/0038 134/6 |
| 2013/0289679 A1 | 10/2013 | Eckhouse et al. |
| 2016/0361573 A1 | 12/2016 | Barthe et al. |

OTHER PUBLICATIONS

Notice of Allowance; U.S. Appl. No. 29/531,918; Mailed Apr. 13, 2016.

"ZIIP"; http://ziipbeauty.com/; retrieved on Jun. 23, 2015.

\* cited by examiner

100

```
                    ┌─ 110
┌─────────────────────────────────────────────┐
│ DELIVERING AN ELECTRIC CURRENT THROUGH AN   │
│ OBJECT IN CONTACT WITH A FIRST ELECTRODE    │
│ AND A SECOND ELECTRODE ON AN APPARATUS      │
└─────────────────────────────────────────────┘
                    │
                    ▼    ┌─ 120
┌─────────────────────────────────────────────┐
│ VIBRATING THE APPARATUS WITH AN ELECTRIC    │
│ MOTOR                                       │
└─────────────────────────────────────────────┘
                    │
                    ▼    ┌─ 130
┌─────────────────────────────────────────────┐
│ CONTROLLING BY A PROCESSOR THE ELECTRIC     │
│ CURRENT DELIVERED BY THE FIRST ELECTRODE    │
│ AND THE SECOND ELECTRODE TO HAVE A SPECIFIC │
│ WAVEFORM, WHEREIN THE PROCESSOR IS          │
│ CONFIGURED TO RECEIVE PROGRAMMABLE          │
│ INSTRUCTIONS TO CONTROL THE ELECTRIC        │
│ CURRENT AND THE ELECTRIC MOTOR              │
└─────────────────────────────────────────────┘
                    │
                    ▼    ┌─ 140
┌─────────────────────────────────────────────┐
│ CONTROLLING A LIGHT EMITTER TO EMIT LIGHT   │
│ WHEN BOTH THE FIRST ELECTRODE AND THE       │
│ SECOND ELECTRODE ARE IN CONTACT WITH THE    │
│ OBJECT                                      │
└─────────────────────────────────────────────┘
                    │
                    ▼    ┌─ 150
┌─────────────────────────────────────────────┐
│ POWERING OFF THE APPARATUS AUTOMATICALLY BY │
│ THE PROCESSOR WHEN THE PROGRAMMABLE         │
│ INSTRUCTIONS COMPLETE EXECUTION             │
└─────────────────────────────────────────────┘
```

FIG. 1

ELECTRICAL CURRENT STIMULATOR APPARATUS

CROSS-REFERENCE TO RELATED APPLICATIONS

This application is a continuation of U.S. application Ser. No. 15/855,282, filed Dec. 27, 2017, which is a continuation of U.S. application Ser. No. 14/587,638, now U.S. Pat. No. 9,861,818, filed Dec. 31, 2014, the entire contents of which each is incorporated herein by reference.

BACKGROUND

Field

This application relates to topical treatments, and more particularly to an electrical current stimulator apparatus for providing topical treatment.

Background

Sending weak electrical currents (typically less than one microampere) into the body has recently become more popular as a new method of rejuvenating the skin and muscles as well as a new technique for physical therapy. The weak electrical currents are commonly used to treat pain, accelerate recovery, and improve cosmetic appearances.

SUMMARY

The following presents a simplified summary of one or more embodiments in order to provide a basic understanding of present technology. This summary is not an extensive overview of all contemplated embodiments of the present technology, and is intended to neither identify key or critical elements of all examples nor delineate the scope of any or all aspects of the present technology. Its sole purpose is to present some concepts of one or more examples in a simplified form as a prelude to the more detailed description that is presented later.

In accordance with one or more aspects of the examples described herein, systems and methods are provided for providing electrical current treatment. In an implementation, a method is provided for providing electrical current treatment. The method includes delivering an electric current through an object in contact with a first electrode and a second electrode on an apparatus. The method further includes vibrating the apparatus with an electric motor. The method further includes controlling by a processor the electric current delivered by the first electrode and the second electrode to have a specific waveform, where the processor is configured to receive programmable instructions to control the electric current and the electric motor.

In a related aspect, the method further includes controlling a light emitter to emit light when both the first electrode and the second electrode are in contact with the object. In another related aspect, the method further includes powering off the apparatus automatically by the processor when the programmable instructions complete execution.

In another implementation, an apparatus is provided for providing electrical current treatment. The apparatus includes an enclosure body with an upper surface and a lower surface located opposite to the upper surface. The apparatus further includes a first electrode and a second electrode on the lower surface for delivering an electric current through an object in contact with the first electrode and the second electrode. The apparatus further includes an electric motor for vibrating the apparatus and a light emitter. The apparatus further includes a processor for controlling the electric current delivered by the first electrode and the second electrode to have a specific waveform, wherein the processor is configured to receive programmable instructions to control the electric current and the electric motor. The apparatus further includes a power button for powering on or off the apparatus and a battery configured to supply power to the first electrode, the second electrode, the processor, and the light emitter.

In yet another implementation, a non-transitory computer-readable medium is provided for providing electrical current treatment. The non-transitory computer-readable medium stores executable instructions which cause a data processing device to deliver an electric current through an object in contact with a first electrode and a second electrode on an apparatus. The data processing device is further caused to vibrate the apparatus with an electric motor. The data processing device is further caused to receive programmable instructions to control the electric current and the electric motor.

BRIEF DESCRIPTION OF THE DRAWINGS

FIG. 1 illustrates an example methodology for providing electrical current treatment;

DETAILED DESCRIPTION

Figure 2:
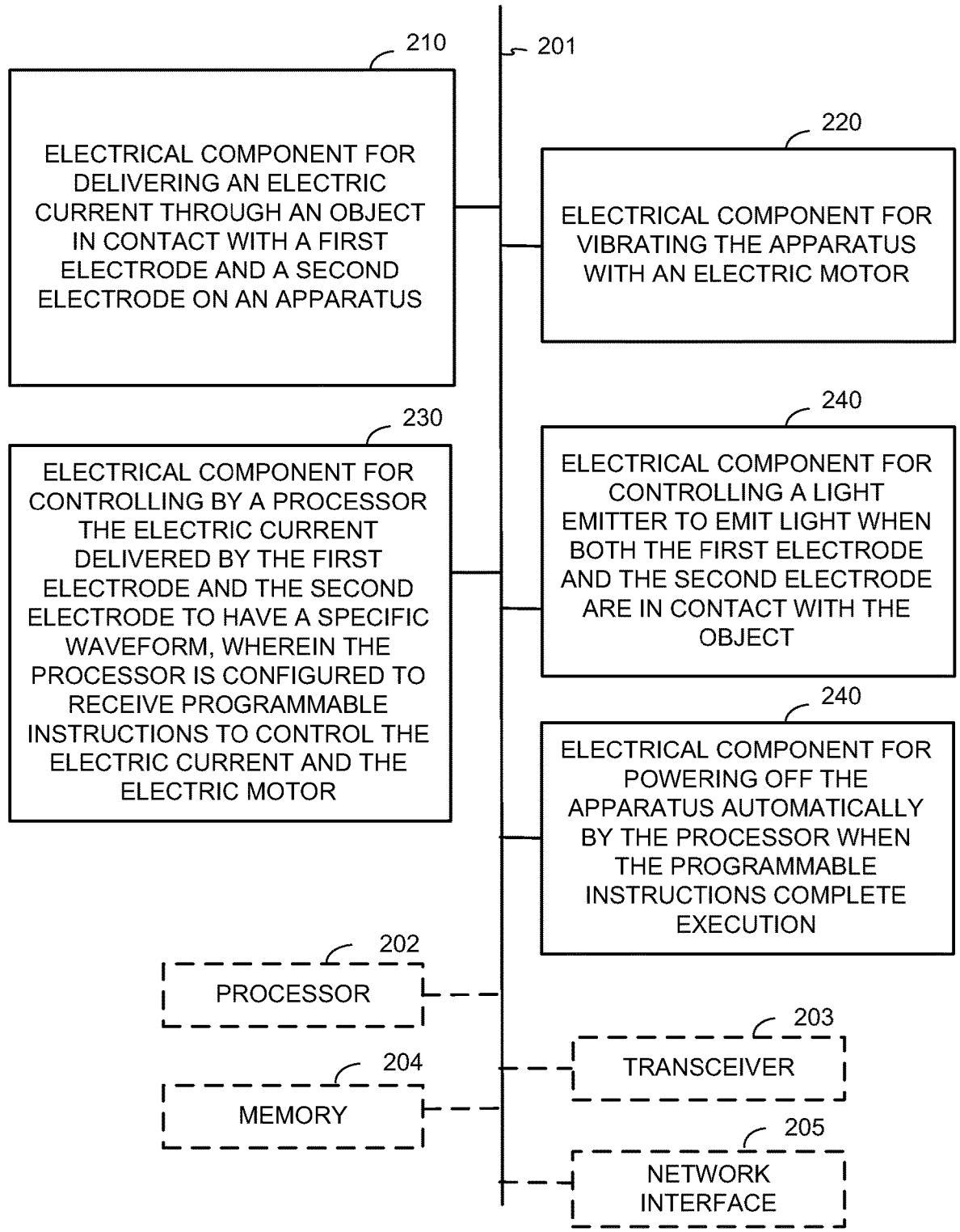
FIG. 2 illustrates an example apparatus providing electrical current treatment in accordance with the methodology of FIG. 1.

Electrotherapy involves the use of electrical stimulator devices to provide various benefits to the human body. For example, a microcurrent electrical neuromuscular stimulator (MENS) is a device that passes low amperage (typically under one microampere) electrical current through the body. MENS devices typically use current amperage that is very close to the current that human bodies produce. Low currents such as microamperes are below the human body's sensation threshold. MENS devices are commonly used for chronic and acute pains, swelling, injuries, Arthritis, and cosmetic purposes.

Another example of an electrical stimulator device is a Transcutaneous electrical nerve stimulation (TENS) device that sends miliampere (one thousand times microampere) electrical currents through the body. TENS devices are commonly used for managing chronic pain. TENS devices utilize biphasic electrical current delivered through electrodes placed on the surface of the skin to stimulate the sensory nerves to block pain signals.

In accordance with certain aspects of the subject technology, an electrical current stimulator apparatus can include an enclosure body with an upper surface and a lower surface located opposite to the upper surface. A user of the apparatus can hold the enclosure body in one of the user's hands.

The apparatus can include a first electrode and a second electrode on the lower surface for delivering an electric current through an object (e.g., the user's body or face) in contact with the first electrode and the second electrode.

The apparatus can include an electric motor for vibrating the apparatus and a light emitter. The vibration can be used to signal to the user to move the apparatus to a different area of the skin.

The apparatus can include a processor for controlling the electric current delivered by the first electrode and the second electrode to have a specific waveform, wherein the processor is configured to receive programmable instructions to control the electric current and the electric motor. The specific waveform can include at least one of a square, sine, triangle, positive/negative ramp, positive/negative unipolar pulse, positive/negative bipolar pulse, trapezoidal alternating current (AC), or other such wave. In a related aspect, the specified waveform can include a direct current (DC) offset. The programmable instructions can be received from a software application for a mobile device, a personal computer, or a tablet device.

In a related aspect, the processor can control a light emitter to emit light when both the first electrode and the second electrode are in contact with the object. The emitted light can signal to the user that the apparatus is correctly placed against the object.

In a related aspect, the apparatus can include a sound output unit for outputting at least one audio clip. The processor can control the sound output unit to output an audio clip from the at least one audio clip, in response to completion of the programmable instructions.

The apparatus can include a power button for powering on or off the apparatus and a battery configured to supply power to the first electrode, the second electrode, the processor, the light emitter, and the sound output unit. The user can press the power button to turn on or off the apparatus to start or stop electrical current stimulation to the user's body or face.

In a related aspect, the processor can automatically execute the programmable instructions when the apparatus is powered on by the power button. In a related aspect, the processor can automatically power off the apparatus when the programmable instructions complete execution.

Various aspects of the present technology are described with reference to the drawings. In the following description, for purposes of explanation, numerous specific details are set forth in order to provide a thorough understanding of one or more aspects. It can be evident, however, that the present technology can be practiced without these specific details. In other instances, well-known structures and devices are shown in block diagram form in order to facilitate describing these aspects. The word "exemplary" is used herein to mean "serving as an example, instance, or illustration." Any embodiment described herein as "exemplary" is not necessarily to be construed as preferred or advantageous over other embodiments.

In accordance with one or more aspects of the implementations described herein, with reference to FIG. 1, a methodology 100 is shown for providing electrical current treatment. The method 100 can involve, at step 110, delivering an electric current through an object in contact with a first electrode and a second electrode on an apparatus. In a related aspect, the first and second electrodes can be located on a surface of the apparatus for delivering an electric current through an object (e.g., the user's body or face) in contact with the first and second electrodes 310. The first electrode and the second electrode can be any electrical conductor configured to make contact with the object. In an example implementation, the first electrode and the second electrode can be substantially identical convex curved surfaces, ideal for smooth movement across the user's body or face.

A processor can control the electric current delivered by the first electrode and the second electrode to have a specific waveform, where the processor is configured to receive programmable instructions to control the electric current and the electric motor. The specific waveform can include at least one of a square, sine, triangle, positive/negative ramp, positive/negative unipolar pulse, positive/negative bipolar pulse, trapezoidal alternating current (AC), or other such wave. In a related aspect, the specific waveform can include a direct current (DC) offset.

The method 100 can involve, at step 120, vibrating the apparatus with an electric motor. In a related aspect, the electric motor can be coupled to the apparatus for vibrating the apparatus. For example, a rotor of the electric motor can be attached to a weight, which causes the electric motor and the apparatus to vibrate when the electric motor spins the rotor. The vibration can be used to signal to the user to move the apparatus to a different area of the object.

The method 100 can involve, at step 130, controlling by a processor the electric current delivered by the first electrode and the second electrode to have a specific waveform, wherein the processor is configured to receive programmable instructions to control the electric current and the electric motor.

The method 100 can optionally involve, at step 140, controlling a light emitter to emit light when both the first electrode and the second electrode are in contact with the object. In a related aspect, the light emitter can include a light emitting diode (LED) or other such low power lighting device. A processor can control the light emitter to emit light when both the first and second electrodes are in contact with the object. The emitted light can signal to a user that the electrical stimulator apparatus is correctly placed against the object.

The method 100 can optionally involve, at step 150, powering off the apparatus automatically by the processor when the programmable instructions complete execution.

In accordance with one or more aspects of the implementations described herein, FIG. 2 illustrates an exemplary apparatus for providing electrical current treatment in accordance with the methodology of FIG. 1. The exemplary apparatus 200 can be configured as a computing device or as a processor or similar device/component for use within. In one example, the apparatus 200 can include functional blocks that can represent functions implemented by a processor, software, or combination thereof (e.g., firmware). In another example, the apparatus 200 can be a system on a chip (SoC) or similar integrated circuit (IC).

In one implementation, the apparatus 200 can include an electrical component or module 210 for delivering an electric current through an object in contact with a first electrode and a second electrode on an apparatus.

The apparatus 200 can include an electrical component 220 for vibrating the apparatus with an electric motor.

The apparatus 200 can include an electrical component 230 for controlling by a processor the electric current delivered by the first electrode and the second electrode to have a specific waveform, wherein the processor is configured to receive programmable instructions to control the electric current and the electric motor.

The apparatus 200 can optionally include an electrical component 240 for controlling a light emitter to emit light when both the first electrode and the second electrode are in contact with the object.

The apparatus 200 can optionally include an electrical component 250 for powering off the apparatus automatically by the processor when the programmable instructions complete execution.

In further related aspects, the apparatus 200 can optionally include a processor component 202. The processor 202 can be in operative communication with the components 210-240 via a bus 201 or similar communication coupling. The processor 202 can effect initiation and scheduling of the processes or functions performed by electrical components 210-240.

In yet further related aspects, the apparatus 200 can include a radio transceiver component 203. A standalone receiver and/or standalone transmitter can be used in lieu of or in conjunction with the transceiver 203. The apparatus 200 can also include a network interface 205 for connecting to one or more other communication devices or the like. The apparatus 200 can optionally include a component for storing information, such as, for example, a memory device/component 204. The computer readable medium or the memory component 204 can be operatively coupled to the other components of the apparatus 200 via the bus 201 or the like. The memory component 204 can be adopted to store computer readable instructions and data for affecting the processes and behavior of the components 210-240, and subcomponents thereof, or the processor 202, or the methods disclosed herein. The memory component 204 can retain instructions for executing functions associated with the components 210-240. While shown as being external to the memory 204, it is to be understood that the components 210-240 can exist within the memory 204. It is further noted that the components in FIG. 2 can include processors, electronic devices, hardware devices, electronic subcomponents, logical circuits, memories, software codes, firmware codes, etc., or any combination thereof.

Persons skilled in the art will appreciate that the functionalities of each component of the apparatus 200 can be implemented in any suitable component of the system or combined in any suitable manner.

Figure 3:
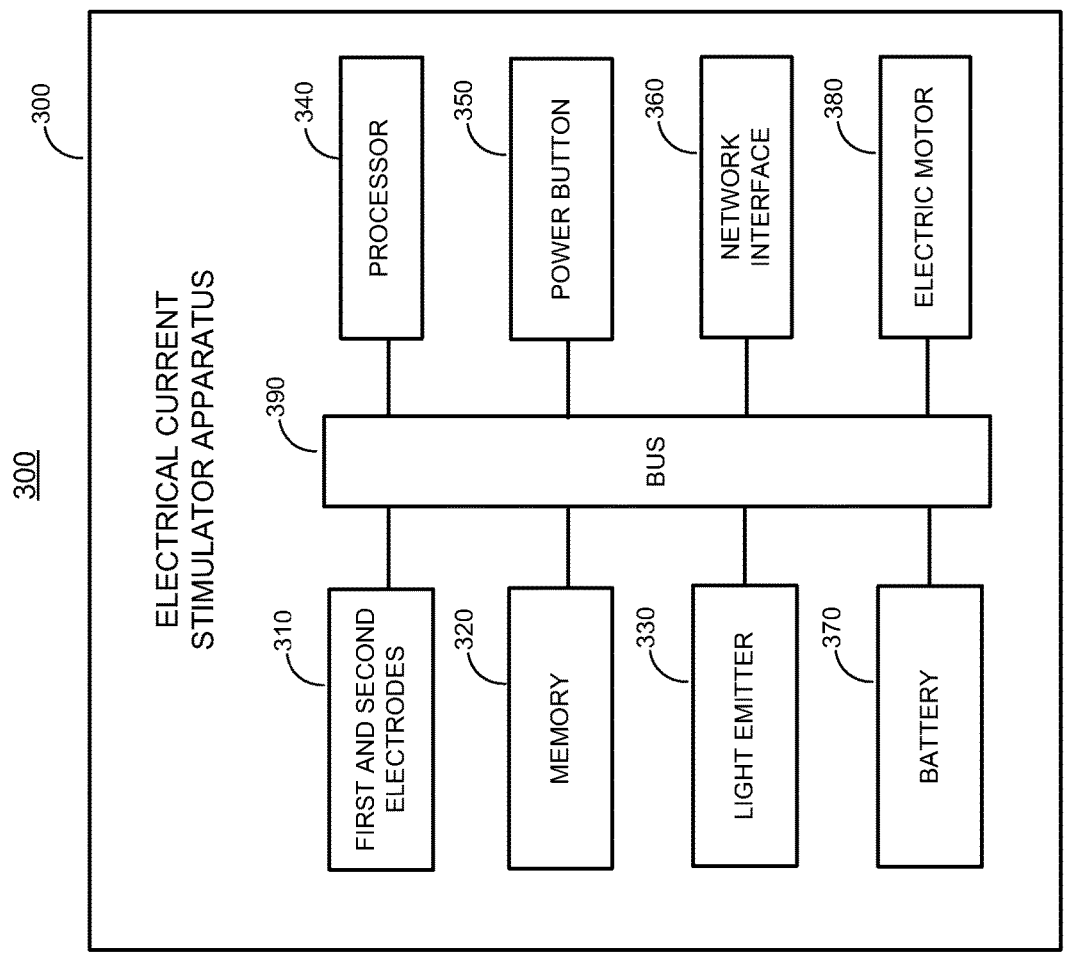
FIG. 3 illustrates an example configuration of components of an electrical stimulator apparatus, according to certain aspects of the subject technology.

FIG. 3 illustrates an example configuration of components of an electrical stimulator apparatus 300, according to certain aspects of the subject technology. The electrical stimulator apparatus 300 can include first and second electrodes 310, a memory 320, a processor 340, a power button 350, a network interface 360, a battery 370, an electric motor 380, and a bus 390. In a related aspect, the electrical stimulator apparatus 300 can further include at least one of a light emitter 330 or a sound output unit (not shown).

The electrical stimulator apparatus 300 can be a handheld device containing a number of different components. The processor (e.g., central processing unit) 340 can retrieve and execute programming instructions stored in the memory 320 (e.g., random-access memory, flash memory, or other storage media). The programing instructions can cause the data processing device 300 to execute the methodology 100 for providing electrical current treatment, as shown in FIG. 1. The processor 340 can be a single CPU with a single processing core, a single CPU with multiple processing cores, or multiple CPUs. The processor 340 and the memory 320 can be integrated into a single unit (e.g., a microcontroller). The bus 390 can transmit instructions and application data between device components such as the first and second electrodes 310, the memory 320, the light emitter 330, the processor 340, the power button 350, the network interface 360, the battery 370, and the electric motor 380.

The first and second electrodes 310 can be located on a surface of the electrical stimulator apparatus 300 for delivering an electric current through an object (e.g., the user's body or face) in contact with the first and second electrodes 310. The first electrode and the second electrode can be any electrical conductor configured to make contact with the object. In an example implementation, the first electrode and the second electrode can be substantially identical convex curved surfaces, ideal for smooth movement across the user's body or face.

The processor 340 can control the electric current delivered by the first electrode and the second electrode to have a specific waveform, where the processor is configured to receive programmable instructions to control the electric current and the electric motor. The specific waveform can include at least one of a square, sine, triangle, positive/negative ramp, positive/negative unipolar pulse, positive/negative bipolar pulse, trapezoidal alternating current (AC), or other such wave. In a related aspect, the specific waveform can include a direct current (DC) offset. The programmable instructions can be received from a software application for a mobile device, a personal computer, or a tablet device. In an example implementation, a particular set of programmable instructions can specify a specific waveform of one microampere that begins with one minute of a square wave, followed by two minutes of a sine wave, followed by five minutes of a triangle wave. It is understood that the specific waveform can include any combination of various waves applied in various time intervals.

The electric motor 380 can be coupled to the electrical stimulator apparatus 300 for vibrating the electrical stimulator apparatus 300. For example, a rotor of the electric motor 380 can be attached to a weight, which causes the electric motor 380 and the electrical stimulator apparatus 300 to vibrate when the electric motor 380 spins the rotor. The vibration can be used to signal to the user to move the electrical stimulator apparatus 300 to a different area of the object.

In a related aspect, the light emitter 330 can include a light emitting diode (LED) or other such low power lighting device. The processor 340 can control the light emitter 330 to emit light when both the first and second electrodes 310 are in contact with the object. The emitted light can signal to the user that the electrical stimulator apparatus 300 is correctly placed against the object.

In a related aspect, the sound output unit can be configured to output at least one audio clip. The at least one audio clip can be stored on the memory 320. In a related aspect, the processor 340 can control the sound output unit to output an audio clip from the at least one audio clip, in response to completion of the programmable instructions. For example, the audio clip can be at least one of a tone, buzz, beep, ring, musical piece, or song. In a related aspect, the processor 340 can control the sound output unit to output another audio clip from the at least one audio clip to signal or instruct the user to move the electrical stimulator apparatus 300 to a different area of the object or that the electrical stimulator apparatus 300 is not correctly placed against the object.

The battery 370 can be configured to supply power to various components of the electrical stimulator apparatus 300, such as the first and second electrodes 310, the processor 340, and the light emitter 330. For example, the battery 370 can include an alkaline battery, a dry cell battery, a lithium battery, a lithium-ion battery, or any other type of disposable or rechargeable battery.

The network interface 350 can include a Universal Serial Bus (USB), Wi-Fi, Bluetooth®, radio frequency, near-field communication (NFC), or any other wired and/or wireless communication interface. Through the network interface 350, the data processing device 300 in certain aspects can communicate with a network, such as the Internet, or with other such devices, such as a mobile phone, tablet, or computer.

In a related aspect, the network interface 350 can include an input socket (not shown) for receiving an electrical connector. The input socket can be configured to receive the programmable instructions through the electrical connector. In a related aspect, the input socket can be configured to receive external power to charge the battery 370. For example, the input socket can be a USB type socket for receiving a USB connector leading to a wall outlet, power supply, laptop, or desktop computer. In another related aspect, the network interface 350 can include a wireless network interface (e.g., Wi-Fi, Bluetooth®, radio frequency, NFC, etc.) for wirelessly receiving the programmable instructions.

The power button 350 can be any type of tactile input component that allows a user to turn on or off the electrical stimulator apparatus 300. For example, the power button 350 can include a physical switch or a capacitive sensor for receiving input from the user. The user can press the power button 350 to turn on or off the electrical stimulator apparatus 300 to start or stop electrical current stimulation. In a related aspect, the processor 340 can automatically execute the programmable instructions when the electrical stimulator apparatus 300 is powered on by the power button 350. In a related aspect, the processor 340 can automatically power off the electrical stimulator apparatus 300 when the programmable instructions complete execution.

Figure 4:
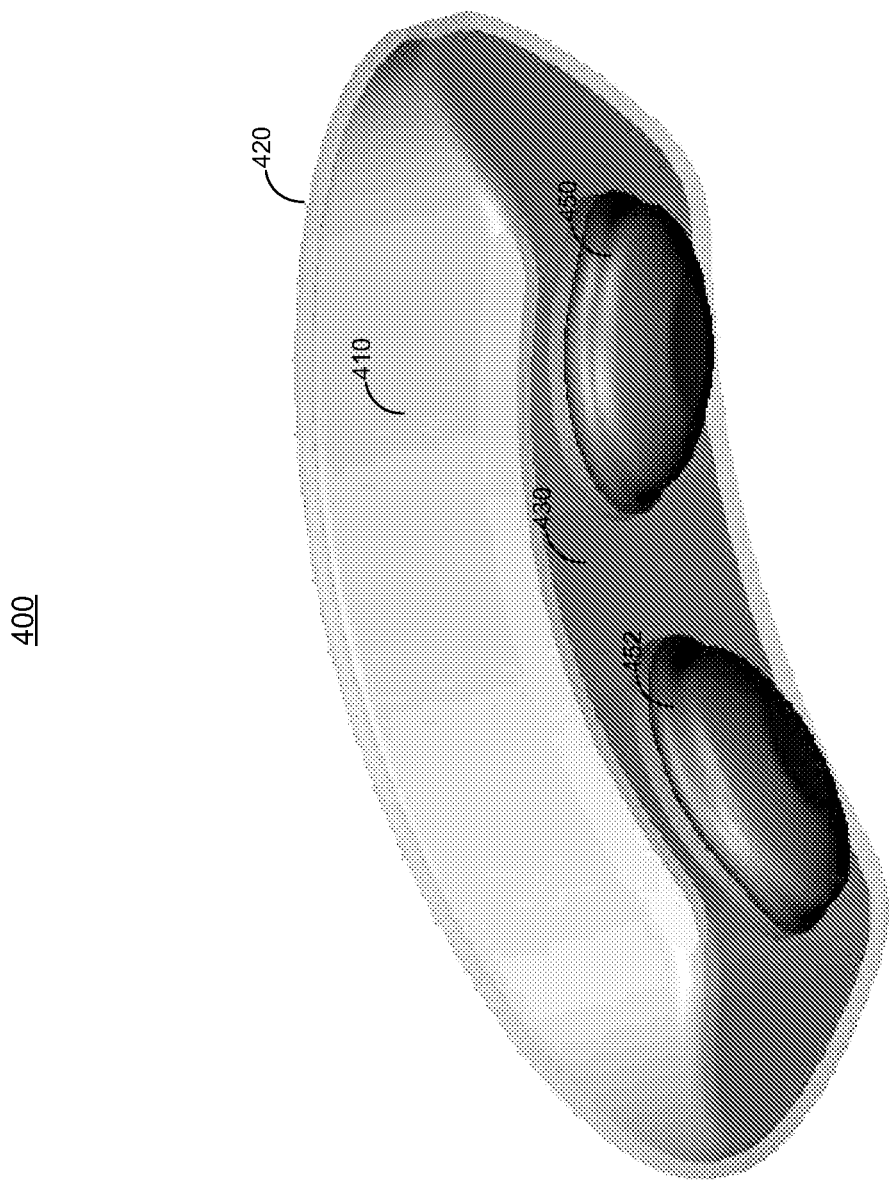
FIG. 4 illustrates an example exterior of an electrical stimulator apparatus, according to certain aspects of the subject technology.

FIG. 4 illustrates an example exterior of an electrical stimulator apparatus 400, according to certain aspects of the subject technology. The electrical stimulator apparatus 400 can include an enclosure body 410 with an upper surface 420 and a lower surface 430 located opposite to the upper surface 420. The enclosure body 410 can be formed from any construction material, such as plastic, metal, wood, fiberglass, rubber, glass, stone, etc. The enclosure body 410 can be rigid or flexible. The enclosure body 410 can be of any shape and size that can be held by one or two human sized hands.

The electrical stimulator apparatus 300 can include a first electrode 450 and a second electrode 452 for delivering an electric current through an object (e.g., the user's body or face, not shown) in contact with the first electrode 450 and the second electrode 452. In an example implementation, the first electrode 450 and the second electrode 452 can be located on the lower surface 430 of the enclosure body 410. The first electrode 450 and the second electrode 452 can be any electrical conductor configured to make contact with the object. In an example implementation, the first electrode 450 and the second electrode 452 can be substantially identical convex curved surfaces, ideal for smooth movement across the user's body or face.

In a related aspect, an electrically conductive gel can be applied on to a surface of the first and second electrodes 450, 452 or on the object to form a conductive layer between the first and second electrodes 450, 452 and the object. The electrically conductive gel can be helpful in facilitating current between the first and second electrodes 450, 452 through the object. In a related aspect, the electrically conductive gel can also have lubricating properties to help facilitate moving the electrical stimulator apparatus 400 over a surface of the object.

Figure 5:
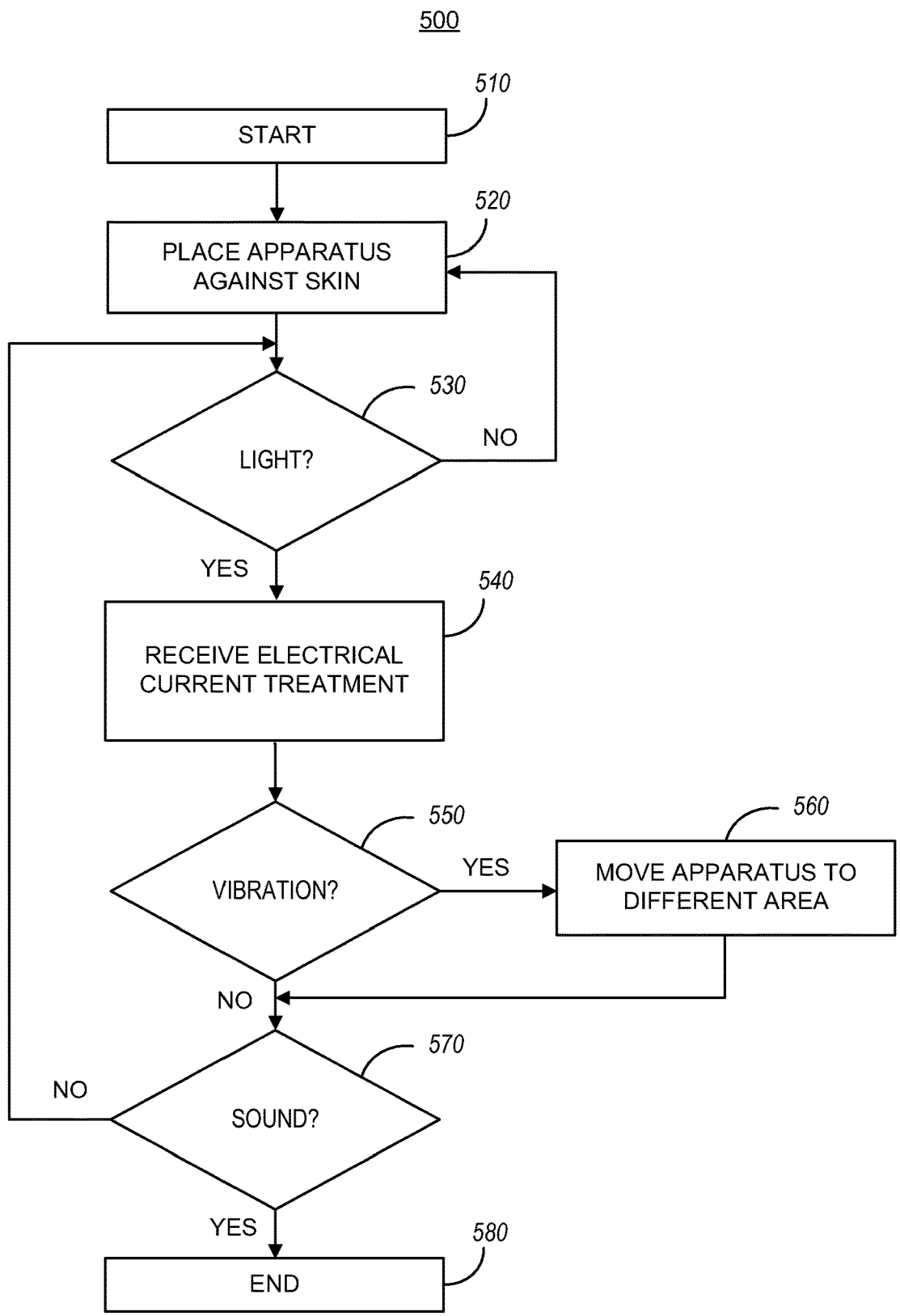
FIG. 5 illustrates an example flowchart of a method for using an electrical stimulator apparatus, according to certain aspects of the subject technology.

FIG. 5 illustrates an example flowchart of a method 500 for using an electrical stimulator apparatus, according to certain aspects of the subject technology. The method 500 can involve, at block 510, a user starting treatment by powering on the electrical stimulator apparatus 300 of FIG. 3. The method 500 can involve, at block 520, placing the first and second electrodes 310 electrical stimulator apparatus 300 against the user's face. The method 500 can involve, at block 530, observing whether the light emitter 330 of the electrical stimulator apparatus 300 is emitting light. If the user does not observe light from the light emitter 330, then the first and second electrodes 310 are not both in contact with the user's face, and the method repeats block 520. If the user does observe light from the light emitter 330, then the first and second electrodes 310 are both in contact with the user's face, and the method continues to block 540.

The method 500 can involve, at block 540, the user receiving electrical current from the first and second electrodes 310 of the electrical stimulator apparatus 300. The method 500 can involve, at block 550, the user observing whether the electrical stimulator apparatus 300 is vibrating. If the user observes the electrical stimulator apparatus 300 vibrating, then the method continues to block 560. The method can involve, at block 560, the user moving the electrical stimulator apparatus 300 to a different location on the user's face. If the user does not observe the electrical stimulator apparatus 300 vibrating, then the electrical stimulator apparatus 300 does not need to be moved yet, and the method continues to block 570.

The method 500 can involve, at block 570, the user observing whether electrical stimulator apparatus 300 is outputting an audio clip from the sound output unit. If the user does not observe the audio clip, then the treatment is not yet finished, and the method repeats block 530. If the user does observe the audio clip, then the treatment is finished, and the method continues to block 580 for termination.

The various implementations can be implemented in a wide variety of operating environments, which in some cases can include one or more user computers, data processing devices, or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Various aspects also can be implemented as part of at least one service or Web service, such as can be part of a service-oriented architecture. Services such as Web services can communicate using any appropriate type of messaging, such as by using messages in extensible markup language (XML) format and exchanged using an appropriate protocol such as SOAP (derived from the "Simple Object Access Protocol"). Processes provided or executed by such services can be written in any appropriate language, such as the Web Services Description Language (WSDL). Using a language such as WSDL allows for functionality such as the automated generation of client-side code in various SOAP frameworks.

Most implementations utilize at least one network that would be familiar to those skilled in the art for supporting communications using any of a variety of commercially-available protocols, such as TCP/IP, OSI, FTP, UPnP, NFS, and CIFS. The network can be, for example, a local area network, a wide-area network, a virtual private network, the Internet, an intranet, an extranet, a public switched telephone network, an infrared network, a wireless network, and any combination thereof In implementations utilizing a Web server, the Web server can run any of a variety of server or mid-tier applications, including HTTP servers, FTP servers, CGI servers, data servers, Java servers, and business map servers. The server(s) also can be capable of executing programs or scripts in response requests from user devices, such as by executing one or more Web applications that can be implemented as one or more scripts or programs written in any programming language, such as Java®, C, C# or C++, or any scripting language, such as Perl, Python, or TCL, as well as combinations thereof The server(s) can also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of implementations, the information can reside in a storage-area network ("SAN") familiar to those skilled in the art. Similarly, any necessary files for performing the functions attributed to the computers, servers, or other network devices can be stored locally and/or remotely, as appropriate. Where a system includes computerized devices, each such device can include hardware elements that can be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system can also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate implementations can have numerous variations from that described above. For example, customized hardware might also be used and/or particular elements might be implemented in hardware, software (including portable software, such as applets), or both. Further, connection to other data processing devices such as network input/output devices can be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various implementations.

The specification and drawings are, accordingly, to be regarded in an illustrative rather than a restrictive sense. It will, however, be evident that various modifications and changes can be made thereunto without departing from the broader spirit and scope of the disclosure as set forth in the claims.

The description of the subject technology is provided to enable any person skilled in the art to practice the various implementations described herein. While the subject technology has been particularly described with reference to the various figures and implementations, it should be understood that these are for illustration purposes only and should not be taken as limiting the scope of the subject technology.

There can be many other ways to implement the subject technology. Various functions and elements described herein can be partitioned differently from those shown without departing from the scope of the subject technology. Various modifications to these implementations will be readily apparent to those skilled in the art, and generic principles defined herein can be applied to other implementations. Thus, many changes and modifications can be made to the subject technology, by one having ordinary skill in the art, without departing from the scope of the subject technology.

A reference to an element in the singular is not intended to mean "one and only one" unless specifically stated, but rather "one or more." The term "some" refers to one or more. All structural and functional equivalents to the elements of the various implementations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

The invention claimed is:

1. A method for providing electrical current treatment of skin by an apparatus having a first electrode and a second electrode extending from a housing and a processor, the method comprising:
   receiving programmable instructions from an external device;
   delivering an electric current to a first area of the skin in contact with the first electrode and the second electrode, wherein the first electrode and the second electrode are substantially identical convex curved surfaces, wherein the electric current is less than one milliampere;

controlling the electric current delivered by the first electrode and the second electrode to have a specific waveform while the first electrode and the second electrode are moved across the first area of the skin to improve cosmetic appearances of the skin; and controlling a notification by the apparatus, the controlling of the notification configured to notify a user to move the apparatus to another area of the skin so that the first electrode and the second electrode are moved across the another area of the skin, wherein at least one of the electric current and the notification is controlled based on the programmable instructions from the external device.

2. The method of claim 1, wherein the notification includes an audio clip.

3. The method of claim 2, wherein the audio clip is output by a sound output unit, wherein the audio clip includes at least one of a tone, buzz, beep, ring, musical piece, and/or song.

4. The method of claim 1, wherein the programmable instructions are received wirelessly through a wireless network interface.

5. The method of claim 4, wherein the wireless network interface is at least one of Wi-Fi, Bluetooth, radio frequency, and near-field communication.

6. The method of claim 1, wherein the programmable instructions are received from a software application for the external device, the external device being at least one of a mobile device, a personal computer, or a tablet device.

7. The method of claim 1, wherein the programmable instructions are received through an electrical connector.

8. The method of claim 1, further comprising:
executing automatically by the processor, when a power button is actuated, the programmable instructions.

9. The method of claim 1, further comprising:
controlling, by the processor, a light emitter to emit light when both the first electrode and the second electrode are in contact with the object.

10. The method of claim 1, wherein the specific waveform includes at least one of a square, sine, triangle, positive/negative ramp, positive/negative unipolar pulse, positive/negative bipolar pulse, trapezoidal alternating current (AC).

11. The method of claim 1, wherein the specified waveform includes a direct current (DC) offset.

12. The method of claim 1, further comprising:
outputting, by the apparatus, a notification in response to completion of the programmable instructions.

13. The method of claim 12, wherein the notification includes an audio clip output through a sound output unit.

14. The method of claim 12, wherein the notification includes automatically adjusting a power setting of the apparatus to an off state.

15. The method of claim 1, wherein the electric current is one of a microcurrent, a nanocurrent, or a picocurrent.

16. The method of claim 1, wherein a lower surface of the apparatus is a concave surface.

17. The method of claim 1, further comprising:
modifying, by the processor, a light emitter when both the first electrode and the second electrode are in contact with the skin.

18. The method of claim 1, wherein the notification includes a vibration.

19. An apparatus for providing electrical current treatment to skin, the apparatus comprising:
an enclosure body;
a first electrode and a second electrode extending from the enclosure body for delivering an electric current through skin in contact with the first electrode and the second electrode, wherein the first electrode and the second electrode are substantially identical convex curved surfaces; and
a processor configured to:
receive programmable instructions from an external device;
control the electric current delivered by the first electrode and the second electrode to have a specific waveform while the first electrode and the second electrode are moved across a first area of the skin to improve cosmetic appearances of the first area of the skin, wherein the electric current is less than one milliampere; and
control a notification by the apparatus, the controlling of the notification configured to notify a user to move the apparatus to another area of the skin so that the first electrode and the second electrode are moved across the another area of the skin,
wherein at least one of the electric current and the notification is controlled based on the programmable instructions from the external device.

20. The apparatus of claim 19, further comprising a sound output unit in communication with the processor, wherein the notification includes an audio clip.

* * * * *